United States Patent [19]

Beach et al.

[11] 4,293,724

[45] Oct. 6, 1981

[54] ALKYLATION OF AROMATICS WITH PROPYLENE AND HIGHER OLEFINS

[75] Inventors: David L. Beach; Thaddeus P. Kobylinski, both of Gibsonia, Pa.

[73] Assignee: Gulf Research & Development Company, Pittsburgh, Pa.

[21] Appl. No.: 151,953

[22] Filed: May 21, 1980

[51] Int. Cl.$^3$ .............................................. C07C 2/66
[52] U.S. Cl. ................................................... 585/457
[58] Field of Search ........................................ 585/457

[56] References Cited

FOREIGN PATENT DOCUMENTS 1060399 7/1959 Fed. Rep. of Germany .
1033161 6/1966 United Kingdom .

OTHER PUBLICATIONS

Bamford, *J. Polym. Sci.*, Part C, No. 4, pp. 1571-1587.

Ichikawa, *J. Chem. Soc. Chem. Comm.*, 1976, pp. 26 & 27, (1978) pp. 566-567.
Bamford et al., *Chem. Abs.*, 57 13961 (1962).
Smith et al, *J. Molecular Catalysis*, 2, pp. 229-241 (1977).

*Primary Examiner*—Curtis R. Davis
*Attorney, Agent, or Firm*—Deane E. Keith; Forrest D. Stine; Joseph J. Carducci

[57] ABSTRACT

An aromatic hydrocarbon is alkylated with an alpha olefin containing three to 10 carbon atoms, or more, by intimately contacting the alpha olefin and the aromatic hydrocarbon with a catalyst produced by contacting (a) a refractory metal oxide/silica support such as alumina/silica wherein the silica content of the support is from two to 95 weight percent and the metal oxide content of the support is from five to 98 percent with (b) a tris(cyclopentadienyl)trinickel dicarbonyl. This process results in the production of significant quantities of alkylated aromatic hydrocarbons.

61 Claims, No Drawings

ALKYLATION OF AROMATICS WITH PROPYLENE AND HIGHER OLEFINS

CROSS-REFERENCES TO RELATED APPLICATIONS

Reference is made to applicants' following U.S. applications:

U.S. Patent application Ser. No. 151,948, filed May 21, 1980, entitled "Refractory Metal Oxide/Silica Supported Nickel Cluster Catalyst".

U.S. Patent application Ser. No. 151,961, filed May 21, 1980, entitled "Process for the Oligomerization of Ethylene".

U.S. Patent application Ser. No. 151,950, filed, May 21, 1980, entitled "Process for the Oligomerization of Propylene and Higher Olefins".

U.S. Patent application Ser. No. 151,951, filed May 21, 1980, entitled "Metal Modified Refractory Metal Oxide/Silica Supported Nickel Cluster Catalyst".

U.S. Patent application Ser. No. 151,952, filed May 21, 1980, entitled "Use of Metal Modified Refractory Metal Oxide/Silica Supported Nickel Cluster Catalyst to Oligomerize Ethylene".

The disclosures of the foregoing applications are hereby incorporated by reference.

FIELD OF THE INVENTION

The present invention relates to the use of a refractory metal oxide/silica supported nickel cluster catalyst to alkylate an aromatic hydrocarbon, such as benzene, with propylene and higher olefins. More particularly, this invention relates to the use of a catalyst obtained by contacting a refractory metal oxide/silica support with a nickel cluster in the alkylation of aromatic hydrocarbons with alpha olefins containing three to 10 carbon atoms, or more.

DESCRIPTION OF THE PRIOR ART

The alkylation of aromatic hydrocarbons with olefins is old in the art. Alkylaromatic compounds are useful as raw materials in the production of polymers and resins. For example, cumene can be oxidized to form phenol, which is used to provide phenolic resins. Thus, a process for producing alkylaromatics provides a method for obtaining useful and economically desirable products.

The processes of the prior art suffer from certain disadvantages, such as the use of high reaction temperatures and the use of expensive catalysts. The use of anhydrous $AlCl_3$ and HF as alkylation catalysts suffer the obvious disadvantages of corrosion and handling difficulties.

A nickel-supported catalyst is described by Masaru Ichikawa in an article entitled "Preparation and Catalytic Activities of Supported Nickel Clusters on a Silica Surface", *J. Chem. Soc., Chem. Comm.* (1976), pages 26 and 27. This article discloses tris(cyclopentadienyl)-trinickel dicarbonyl and other nickel cluster compounds deposited on silica gel or Vycor glass No. 7930 followed by heating at 120° C. as catalysts for olefin hydrogenation and for the "oxo" reaction. Vycor glass No. 7930 is understood to be 95.6 weight percent silica, 1.0 weight percent alumina, 2.25 weight percent boric acid, the remaining 0.25 weight percent being unidentified contaminants.

SUMMARY OF THE INVENTION

It has now been found that alpha olefins containing three to 10 carbon atoms, or more, can be used to alkylate aromatic hydrocarbons by intimately contacting the alpha olefin and the aromatic hydrocarbon with a catalyst produced by contacting (a) a refractory metal oxide/silica support such as alumina/silica wherein the silica content of the support is from about 2 to about 95 weight percent and the metal oxide content of the support is from about 5 to about 98 percent with (b) a tris(cyclopentadienyl)trinickel dicarbonyl. The process is characterized by ease of catalyst handling, low operating temperatures and pressures, and the production of significant amounts of alkylated aromatic hydrocarbons.

The tris(cyclopentadienyl)trinickel dicarbonyl used herein has the structure:

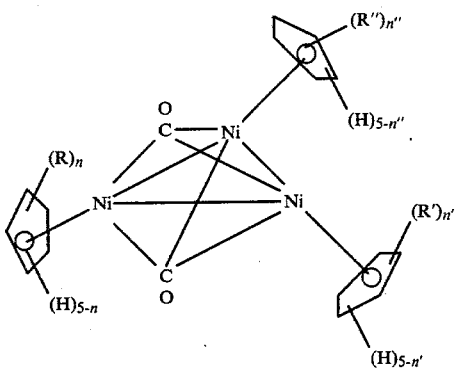

wherein R, R' and R" can be the same or different $C_1$ to $C_{20}$ inclusive, hydrocarbon radicals, and n, n' and n" can be the same or different integers of 0 to 5, inclusive. The R, R' and R" hydrocarbon radicals can be saturated or unsaturated, they can include aliphatic, alicyclic and aromatic radicals such as methyl, ethyl, propyl, butyl, pentyl, cyclopentyl, cyclohexyl, allyl, phenyl and naphthyl radicals. One or more of the cyclopentadienyl moieties in the foregoing tris(cyclopentadienyl)trinickel dicarbonyl can be substituted so as to form an indenyl moiety or a fluorenyl moiety.

Specific examples of nickel clusters which can be used include:
tris(cyclopentadienyl)trinickel dicarbonyl,
tris(methylcyclopentadienyl)trinickel dicarbonyl,
(methylcyclopentadienyl)bis(cyclopentadienyl)-
    trinickel dicarbonyl,
bis(methylcyclopentadienyl)(cyclopentadienyl)-
    trinickel dicarbonyl,
tris(pentamethylcyclopentadienyl)trinickel dicarbonyl,
(pentamethylcyclopentadienyl)bis(cyclopentadienyl)-
    trinickel dicarbonyl,
bis(pentamethylcyclopentadienyl)(cyclopentadienyl)-
    trinickel dicarbonyl,
(methylcyclopentadienyl)bis(pentamethylcyclopen-
    tadienyl)trinickel dicarbonyl,
bis(methylcyclopentadienyl)(pentamethylcyclopen-
    tadienyl)trinickel dicarbonyl,
tris(ethylcyclopentadienyl)trinickel dicarbonyl,
(ethylcyclopentadienyl)bis(cyclopentadienyl)trinickel
    dicarbonyl,
bis(ethylcyclopentadienyl)(cyclopentadienyl)trinickel
    dicarbonyl, tris(n-propylcyclopentadienyl)trinickel dicarbonyl,
tris(iso-propylcyclopentadienyl)trinickel dicarbonyl,
tris(butylcyclopentadienyl)trinickel dicarbonyl,
tris(pentylcyclopentadienyl)trinickel dicarbonyl,
tris(indenyl)trinickel dicarbonyl,
(indenyl)bis(cyclopentadienyl)trinickel dicarbonyl,
bis(indenyl)(cyclopentadienyl)trinickel dicarbonyl,
(indenyl)bis(methylcyclopentadienyl)trinickel dicarbonyl,
bis(indenyl)(methylcyclopentadienyl)trinickel dicarbonyl,
(indenyl)bis(pentamethylcyclopentadienyl)trinickel dicarbonyl,
bis(indenyl)(pentamethylcyclopentadienyl)trinickel dicarbonyl,
wherein the indenyl moiety has the structure:

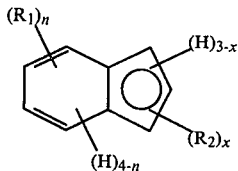

wherein ($R_1$) and ($R_2$) are the same or different $C_1$ to to $C_{10}$ hydrocarbon radicals, n is an integer of 0 to 4, and x is an integer of 0 to 3,
tris(fluorenyl)trinickel dicarbonyl,
(fluorenyl)bis(cyclopentadienyl)trinickel dicarbonyl,
bis(fluorenyl)(cyclopentadienyl)trinickel dicarbonyl,
(fluorenyl)bis(methylcyclopentadienyl)trinickel dicarbonyl,
bis( fluorenyl)methylcyclopentadienyl)trinickel dicarbonyl,
(fluorenyl)bis(pentamethylcyclopentadienyl)trinickel dicarbonyl,
bis(fluorenyl)(pentamethylcyclopentadienyl)trinickel dicarbonyl,
wherein the fluorenyl moiety has the structure:

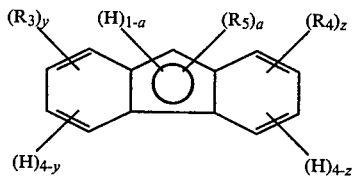

wherein ($R_3$), ($R_4$) and ($R_5$) can be the same or different $C_1$ to $C_{10}$ hydrocarbon radicals; y and z can be the same or different integers of 0 to 4; and a is 0 or 1. The ($R_1$), ($R_2$), ($R_3$), ($R_4$) and ($R_5$) hydrocarbon radicals can be the same or different, saturated or unsaturated and include the hydrocarbon radicals as described for R, R' and R".

The metal oxide associated with the silica in the support may be defined by the formula $M_xO_y$ wherein M is aluminum, magnesium, zirconium or thorium, x is an integer of from 1 to 2 and y is an integer of from 1 to 3. Specific examples of such compounds include $Al_2O_3$, MgO, $ZrO_2$, $ThO_2$, etc.

DESCRIPTION OF THE PREFERRED EMBODIMENTS

The alpha olefins having from three to 10 carbon atoms, or more, that can be used in accordance with the practice of this invention include propylene, 1-butene, 1-hexene, 1-octene, 1-decene, etc. Aromatic hydrocarbons that can be alkylated in accordance with the practice of this invention can have from six to 14 carbon atoms, preferably from six to 10 carbon atoms. Specific examples of aromatic hydrocarbons that can be used include benzene, toluene, o-, m- and p-xylenes, mesitylene, ethyl benzene, n-propylbenzene, cumene, n-butylbenzene, sec-butylbenzene, isobutylbenzene, naphthalene, anthracene, phenanthrene, etc.

In alkylating the aromatic hydrocarbon with the alpha olefin, as defined above, they are contacted with each other in the presence of the defined catalyst at a temperature in the range of about 20° to about 250° C., preferably about 20° to about 170° C., and a pressure of about one to about 50 atmospheres, or higher, preferably from about one to about 30 atmospheres, for about 10 minutes to about 12 hours, or longer, but preferably from about 0.5 to about four hours. Thus, the alpha olefin can be brought into contact with a slurry composed of said catalyst and said aromatic hydrocarbon, as defined above. The amount of catalyst required can range from about 0.1 milligram to about 1000 milligrams of nickel in the catalyst per mole of alpha olefin, preferably from about 1.0 milligram to about 100 milligrams of nickel in the catalyst per mole of alpha olefin.

In case the aromatic hydrocarbon being alkylated is a solid, for example, anthracene, the reaction can be conducted in the presence of an inert solvent, such as aliphatic and alicyclic hydrocarbons. Aliphatic solvents that can be used can have from four to 14 carbon atoms, or even higher, preferably from five to 10 carbon atoms. Alicyclic solvents that can be used can have from five to 14 carbon atoms, or even higher, preferably from five to 10 carbon atoms. Specific examples of such solvents that can be used include isobutane, n-pentane, isopentane, n-hexane, isohexane, dimethylbutane, n-heptane, methylhexane, n-octane, isooctane, n-nonane, n-decane, n-dodecane, cyclopentane, methylcyclopentane, cyclohexane, methylcyclohexane, ethylcyclohexane, cycloheptane, cyclooctane, cyclononane, cyclodecane, etc.

The supported nickel catalyst, the aromatic hydrocarbon and the alpha olefin can be contacted in any suitable reaction vessel, such as an autoclave or similar reaction vessel, provided with suitable agitation means. Preferably, the reaction vessel is purged with an inert gas such as argon or nitrogen before the catalyst, aromatic hydrocarbon and alpha olefin are added.

At the end of the reaction period, the contents of the reaction vessel are cooled to a temperature of about −10° to about 50° C., preferably about 20° to about 50° C., after which any unreacted propylene or butene, if present, are vented from the system and the pressure is reduced to about one to about five atmospheres. The reactor contents are then filtered to recover the solid catalyst. The solvent and the alkylated aromatic products can be separated and isolated, if desired, by conventional methods, such as fractional distillation, extraction, selective adsorption, etc. The catalyst and any unreacted alpha olefin and aromatic hydrocarbon can be recycled to the reaction vessel.

A suitable support for the catalyst composition for use in the process of this invention is a metal oxide/silica support wherein the silica content is from about 2 to about 95 weight percent and the metal oxide content is from about 5 to about 98 weight percent. Preferably, the support comprises from about 15 to about 92 weight percent silica and about 10 to about 85 weight percent metal oxide; and most preferably from about 80 to about 92 weight percent silica and from about 10 to about 20 weight percent metal oxide. The metal oxide/silica supports include synthetic materials as well as acid-treated clays or even the crystalline alumina silicates known as molecular sieves, so long as the silica and alumina contents are within the ranges specified. Thus, any of the commercially available metal oxide/silicas having the proper silica to metal oxide ratios can suitably be used to prepare the compositions of this invention. The preferred alumina/silicas are coprecipitated from aqueous or alcoholic solutions of a silicate such as sodium silicate or silicic acid and an aluminum salt such as aluminum nitrate, aluminum sulfate or aluminum chloride. For example, an aqueous solution of silicic acid and aluminum nitrate produces a coprecipitate when treated with ammonium hydroxide at a controlled pH of about 8. Differing physical properties of the co-precipitates result by varying the pH during precipitation. The precipitates are an intimate comixture of silicon and aluminum oxides.

Preferably, the support is calcined prior to contact with the nickel cluster as by heating at a temperature of from about 200° C. to about 800° C. and, more preferably, from about 450° C. to about 650° C. for a period of from about one to about 24 hours, or even longer, but preferably about four to about 12 hours. The calcining operation can be conducted in air, but is preferably conducted in an inert atmosphere such as in a stream of argon or nitrogen. Following the calcining operation, the support is cooled slowly in an inert atmosphere and stored in the absence of air.

The calcined support is then contacted in the absence of air with the nickel cluster, that is, a tris(cyclopentadienyl)trinickel dicarbonyl. The nickel cluster defined by the chemical formula $(\eta^5-C_5H_5)_3Ni_3(CO)_2$, wherein $\eta$ is the Greek letter eta, used herein, can be prepared by the method of E. O. Fischer et al. described in *Chem. Ber.*, 91, 1725 (1958). This compound is a solid at room temperature and is not sensitive to air. The structure of the nickel cluster consists of a triangle of nickel atoms with a cyclopentadienyl ligand bonded to each nickel in a pentahapto fashion and two triply-bridging carbon monoxide ligands. This complex has the structure represented above when each of n, n' and n" has a value of O.

One method of contacting the support with the nickel cluster is to use a solution of the nickel cluster in a liquid hydrocarbon solvent which is non-reactive. Examples of such solvents include pentane, hexane, heptane, cyclopentane, cyclohexane, benzene, toluene, and xylene. The amount of nickel cluster used is not critical and can vary widely as long as the nickel content of the product obtained from the reaction of the nickel cluster with the support is within the range of about 0.001 to about five weight percent, preferably within the range of about 0.05 to about two weight percent.

The nickel cluster and the support are contacted at a temperature of from about 20° to about 200° C. for a period of about 10 minutes to about 12 hours and, more preferably, for about 15 minutes to about one hour at a temperature of from about 20° to about 100° C. The temperature and time can vary widely depending upon the solubility-temperature profile of the solvent and nickel cluster. They can be contacted in any suitable reaction vessel such as an autoclave.

The nickel cluster has a low solubility in certain aliphatic and alicyclic solvents such as heptane and cyclohexane. This may result in a very slow transfer and/or an incomplete transfer of the nickel cluster from solution to the support. Thus, when using such solvents, a different method of contacting the nickel cluster and the support is preferably used. According to this method, instead of adding the nickel cluster as a solution to the reaction chamber, it is charged as a solid with the support. After purging the reaction chamber with an inert gas such as argon or nitrogen, the solvent is then added to the reaction chamber.

Following the necessary contact time to effect deposition of the nickel cluster onto the support, the resultant catalyst composition can be separated from the solvent diluent and stored, preferably in an inert atmosphere, until ready for use. Separation can be accomplished by conventional techniques such as filtration, centrifugation, and decantation. The catalyst composition can be dried in an inert atmosphere. Alternatively, the catalyst composition can be used in the solvent diluent in which it was prepared if a non-aromatic solvent diluent was used, i.e., the aromatic hydrocarbon may serve as the solvent diluent in the deposition of the nickel cluster on the support and then as a reactant in the alkylation reaction.

It is preferred to activate or preactivate the catalyst composition prior to contact with the alpha olefin and aromatic hydrocarbon unless temperatures exceeding 100° C. were used in the reaction of the nickel cluster with the support in which case the activation or preactivation is unnecessary. Activation and preactivation of the catalyst can be accomplished by heating it in an inert atmosphere at a temperature between about 70° and about 200° C., preferably about 100° to about 170° C., for from about five minutes to about 4 hours, or longer, but preferably about 20 minutes to about one hour. The term "activation" as used herein refers to an operation performed in situ in the alkylation reactor prior to the addition of the alpha olefin and aromatic hydrocarbon; and the term "preactivation" refers to an operation performed external to the alkylation reactor.

The following examples illustrate the best mode contemplated for carrying out this invention. All percentages are by weight unless otherwise indicated.

Example 1

An alumina/silica support comprising 87 weight percent silica and 12 weight percent alumina was calcined under argon at 550° C. for 5 hours. The support had a surface area of 425–450 m.²/g. Subsequently, 2.68 grams of this support and 0.0077 gram of solid tris(cyclopentadienyl)trinickel dicarbonyl under argon were charged to a 300 cc. autoclave. Purging was accomplished with 3 successive pressure-vent cycles using argon. Benzene (50 ml.) was weighed and syringed into the autoclave under argon. The contents were stirred at ambient temperature for 2.0 hours and were then rapidly heated to 150° C. and maintained at that temperature for 30 minutes. Propylene was then added to a total pressure of 100 psig (690 kPa) and maintained at this temperature and pressure for 1.0 hour. The autoclave was then rapidly cooled to 5° C. and the liquid contents were collected in a tared, cooled bottle and analyzed immediately by gas chromatography. The results of these experiments are shown in Table I.

TABLE I

| | Selectivity, percent |
|---|---|
| C-6 olefins | 1 |

TABLE I-continued

| | Selectivity, percent |
|---|---|
| C-9 olefins | 0.5 |
| Cumene | 26.5 |
| Diisopropylbenzenes | 37 |
| C-12 (olefins plus alkylated benzenes, excluding diisopropylbenzenes) | 35.5 |

Thus, it is seen from Table I that significant amounts of mono- and dialkylated benzenes are produced.

Example 2

The process of Example 1 was repeated substituting 1-hexene for propylene at one atmosphere pressure and using 2.42 grams of support. The alkylation reaction was run for 4.7 hours. The results of analysis of the product obtained are reported in Table II.

TABLE II

| | Selectivity, percent |
|---|---|
| C-12 olefins | 12 |
| 3-phenylhexane | 23 |
| 2-phenylhexane | 41 |
| (C-12)-benzene | 6 |
| ≧C-18 (olefins + alkylated benzenes) | 18 |

Thus, it is seen that the benzene is alkylated with the 1-hexene to provide significant amounts of alkylated benzene.

Although the invention has been described in considerable detail with particular reference to certain preferred embodiments thereof, variations and modifications can be effected within the spirit and scope of the invention as described hereinbefore, and as defined in the appended claims.

We claim:

1. A process for alkylating an aromatic hydrocarbon with an alpha olefin which comprises contacting an alpha olefin having at least three carbon atoms and an aromatic hydrocarbon with a catalyst composition obtained by contacting (a) a refractory metal oxide/silica support wherein the silica content of said support is from about 2 to about 95 weight percent and the metal oxide content of said support is from about 5 to about 98 weight percent with (b) a tris(cyclopentadienyl)trinickel dicarbonyl.

2. A process as defined in claim 1 wherein said tris(-cyclopentadienyl)trinickel dicarbonyl has the structure:

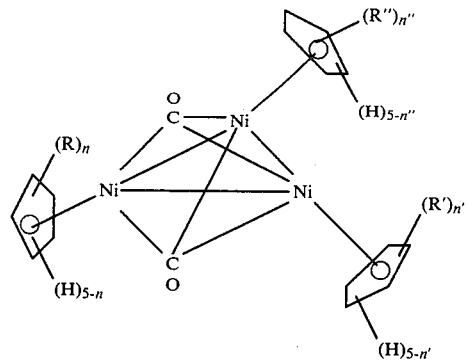

wherein R, R' and R" are the same or different $C_1$ to $C_{20}$ hydrocarbon radicals and n, n' and n" can be the same or different integers of 0 to 5, inclusive.

3. A process as defined in claim 2 wherein the metal oxide component of said support has the formula $M_xO_y$, wherein M is aluminum, magnesium, zirconium or thorium, x is an integer of from 1 to 2 and y is an integer of from 1 to 3.

4. A process as defined in claim 3 wherein the metal oxide in said support is alumina.

5. A process as defined in claim 1 wherein the silica content in said support is from about 15 to about 92 weight percent and the metal oxide content in said support is from about 10 to about 85 weight percent.

6. A process as defined in claim 1 wherein the silica content in said support is from about 80 to about 92 weight percent and the metal oxide content in said support is from about 10 to about 20 weight percent.

7. A process as defined in claim 4 wherein the silica content in said support is from about 15 to about 92 weight percent and the alumina content in said support is from about 10 to about 85 weight percent.

8. A process as defined in claim 4 wherein the silica content in said support is from about 80 to about 92 weight percent and the alumina content in said support is from about 10 to about 20 weight percent.

9. A process as defined in claim 4 wherein the silica content in said support is about 87 weight percent and the alumina content in said support is about 12 weight percent.

10. A process as defined in claim 4 wherein the silica content in said support is about 75 weight percent and the alumina content in said support is about 25 weight percent.

11. A process as defined in claim 1 wherein said tris(-cyclopentadienyl)trinickel dicarbonyl is defined by the chemical formula $(\eta^5\text{-}C_5H_5)_3Ni_3(CO)_2$.

12. A process as defined in claim 2 wherein said tris(-cyclopentadienyl)trinickel dicarbonyl is defined by the chemical formula $(\eta^5\text{-}C_5H_5)_3Ni_3(CO)_2$.

13. A process as defined in claim 3 wherein said tris(-cyclopentadienyl)trinickel dicarbonyl is defined by the chemical formula $(\eta^5\text{-}C_5H_5)_3Ni_3(CO)_2$.

14. A process as defined in claim 4 wherein said tris(-cyclopentadienyl)trinickel dicarbonyl is defined by the chemical formula $(\eta^5\text{-}C_5H_5)_3Ni_3(CO)_2$.

15. A process as defined in claim 5 wherein said tris(-cyclopentadienyl)trinickel dicarbonyl is defined by the chemical formula $(\eta^5\text{-}C_5H_5)_3Ni_3(CO)_2$.

16. A process as defined in claim 6 wherein said tris(cyclopentadienyl)trinickel dicarbonyl is defined by the chemical formula $(\eta^5\text{-}C_5H_5)_3Ni_3(CO)_2$.

17. A process as defined in claim 7 wherein said tris(cyclopentadienyl)trinickel dicarbonyl is defined by the chemical formula $(\eta^5\text{-}C_5H_5)_3Ni_3(CO)_2$.

18. A process as defined in claim 8 wherein said tris(cyclopentadienyl)trinickel dicarbonyl is defined by the chemical formula $(\eta^5\text{-}C_5H_5)_3Ni_3(CO)_2$.

19. A process as defined in claim 9 wherein said tris(cyclopentadienyl)trinickel dicarbonyl is defined by the chemical formula $(\eta^5\text{-}C_5H_5)_3Ni_3(CO)_2$.

20. A process as defined in claim 10 wherein said tris(cyclopentadienyl)trinickel dicarbonyl is defined by the chemical formula $(\eta^5\text{-}C_5H_5)_3Ni_3(CO)_2$.

21. A process as defined in claim 1 wherein said support is calcined, prior to said contact with said tris(cyclopentadienyl)trinickel dicarbonyl at a temperature from about 200° to about 800° C. for about one to about 24 hours.

22. A process as defined in claim 1 wherein said contact between said support and said tris(cyclopentadienyl)trinickel dicarbonyl is conducted in the absence of air at a temperature of about 20° to about 200° C.

23. A process as defined in claim 1 wherein a solution of said tris(cyclopentadienyl)trinickel dicarbonyl is contacted with said support.

24. A process as defined in claim 23 wherein said solution is a benzene solution.

25. A process as defined in claim 23 wherein said solution is a cyclohexane solution.

26. A process as defined in claim 1 wherein the nickel content of said catalyst composition is from about 0.001 to about five weight percent.

27. A process as defined in claim 1 wherein the nickel content of said catalyst composition is from about 0.05 to about two weight percent.

28. A process as defined in claim 14 wherein the nickel content of said catalyst composition is from about 0.001 to about five weight percent.

29. A process as defined in claim 14 wherein the nickel content of said catalyst composition is from about 0.05 to about two weight percent.

30. A process as defined in claim 1 wherein said contact between said support and said tris(cyclopentadienyl)trinickel dicarbonyl is effected at a temperature from about 20° to about 200° C. for about 10 minutes to about 12 hours.

31. A process as defined in claim 1 wherein said contact between said support and said tris(cyclopentadienyl)trinickel dicarbonyl is effected at a temperature from about 20° to about 100° C. for about 15 minutes to about one hour.

32. A process as defined in claim 14 wherein said contact between said support and said tris(cyclopentadienyl)trinickel dicarbonyl is effected at a temperature from about 20° to about 200° C. for about 10 minutes to about 12 hours.

33. A process as defined in claim 14 wherein said contact between said support and said tris(cyclopentadienyl)trinickel dicarbonyl is effected at a temperature from about 20° to about 100° C. for about 15 minutes to about one hour.

34. A process as defined in claim 1 wherein the solid tris(cyclopentadienyl)trinickel dicarbonyl is contacted with said support and a hydrocarbon solvent is then added.

35. A process as defined in claim 34 wherein said hydrocarbon solvent is benzene.

36. A process as defined in claim 34 wherein said hydrocarbon solvent is cyclohexane.

37. A process as defined in claim 1 wherein said catalyst is activated or preactivated by heating at a temperature of about 70° to about 200° C. for about five minutes to about four hours.

38. A process as defined in claim 1 wherein said catalyst is activated or preactivated by heating at a temperature of about 100° to about 170° C. for about twenty minutes to about one hour.

39. A process as defined in claim 14 wherein said catalyst is activated or preactivated by heating at a temperature of about 70° to about 200° C. for about five minutes to about four hours.

40. A process as defined in claim 14 wherein said catalyst is activated or preactivated by heating at a temperature of about 100° to about 170° C. for about twenty minutes to about one hour.

41. A process as defined in claim 1 wherein said aromatic hydrocarbon, alpha olefin and catalyst composition are contacted at a temperature of from about 20° to about 250° C. and a pressure of from about one to about 50 atmospheres for about 10 minutes to about 12 hours.

42. A process as defined in claim 1 wherein said aromatic hydrocarbon, alpha olefin and catalyst composition are contacted at a temperature of from about 20° to about 170° C. and a pressure of from about one to about 30 atmospheres for about 0.5 to about four hours.

43. A process as defined in claim 4 wherein said aromatic hydrocarbon, alpha olefin and catalyst composition are contacted at a temperature of from about 20° to about 250° C. and a pressure of from about one to about 50 atmospheres for about 10 minutes to about 12 hours.

44. A process as defined in claim 4 wherein said aromatic hydrocarbon, alpha olefin and catalyst composition are contacted at a temperature of from about 20° to about 170° C. and a pressure of from about one to about 30 atmospheres for about 0.5 to about four hours.

45. A process as defined in claim 14 wherein said aromatic hydrocarbon, alpha olefin and catalyst composition are contacted at a temperature of from about 20° to about 250° C. and a pressure of from about one to about 50 atmospheres for about 10 minutes to about 12 hours.

46. A process as defined in claim 14 wherein said aromatic hydrocarbon, alpha olefin and catalyst composition are contacted at a temperature of from about 20° to about 170° C. and a pressure of from about one to about 30 atmospheres for about 0.5 to about four hours.

47. A process as defined in claim 1 wherein said alpha olefin contains three to 10 carbon atoms.

48. A process as defined in claim 47 wherein said alpha olefin is propylene.

49. A process as defined in claim 47 wherein said alpha olefin is 1-hexene.

50. A process as defined in claim 4 wherein said alpha olefin contains three to 10 carbon atoms.

51. a process as defined in claim 50 wherein said alpha olefin is propylene.

52. A process as defined in claim 50 wherein said alpha olefin is 1-hexene.

53. A process as defined in claim 14 wherein said alpha olefin contains three to 10 carbon atoms.

54. A process as defined in claim 53 wherein said alpha olefin is propylene.

55. A process as defined in claim 53 wherein said alpha olefin is 1-hexene.

56. A process as defined in claim 1 wherein said catalyst composition is present in an amount sufficient to provide about 0.1 mg. to about 1.0 g. of nickel per mole of alpha olefin.

57. A process as defined in claim 1 wherein said catalyst composition is present in an amount sufficient to provide about 1.0 mg. to about 0.1 g. of nickel per mole of alpha olefin.

58. A process as defined in claim 4 wherein said catalyst composition is present in an amount sufficient to provide about 0.1 mg. to about 1.0 g. of nickel per mole of alpha olefin.

59. A process as defined in claim 4 wherein said catalyst composition is present in an amount sufficient to provide about 1.0 mg. to about 0.1 g. of nickel per mole of alpha olefin.

60. A process as defined in claim 14 wherein said catalyst composition is present in an amount sufficient to provide about 0.1 mg. to about 1.0 g. of nickel per mole of alpha olefin.

61. A process as defined in claim 14 wherein said catalyst composition is present in an amount sufficient to provide about 1.0 mg. to about 0.1 g. of nickel per mole of alpha olefin.

* * * * *